United States Patent
Ziel et al.

(10) Patent No.: US 6,224,557 B1
(45) Date of Patent: May 1, 2001

(54) ULTRASONIC METHOD USING ADAPTIVE CLUTTER FILTER TO REMOVE TISSUE WALL MOTION

(75) Inventors: J Mark Ziel, North Andover; Karl E Thiele, Andover, both of MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/497,579

(22) Filed: Feb. 3, 2000

(51) Int. Cl.[7] .................................................. A61B 8/00
(52) U.S. Cl. .................................. 600/455; 600/458
(58) Field of Search ............................... 600/455, 453, 600/454, 437, 443, 438, 458

(56) References Cited

U.S. PATENT DOCUMENTS

| | | | |
|---|---|---|---|
| 5,456,257 | 10/1995 | Johnson et al. | 128/662.02 |
| 5,709,210 | * 1/1998 | Green et al. | 600/453 |
| 5,833,613 | 11/1998 | Averkiou et al. | 600/440 |
| 6,110,117 | * 8/2000 | Ji et al. | 600/453 |
| 6,146,331 | * 11/2000 | Wong | 600/454 |

* cited by examiner

Primary Examiner—Marvin M. Lateef
Assistant Examiner—Maulin Patel

(57) ABSTRACT

The method of the invention controls an ultrasound system that implements a clutter filter, to derive parameters such as blood flow velocity, echo power and/or echo amplitude data from an anatomical region of interest (ROI) and into which a contrast agent has been introduced. The method initially transmits an ensemble of N ultrasound beams along a common azimuth and elevation into the ROI to cause destruction of the contrast agent lying along the azimuth. Estimated wall motion velocity data is then derived for the tissue wall region through use of selected echo signal data derived from a subset of the N ultrasound beams of the ensemble, the subset excluding echo signal data from a first M of the N ultrasound beams or any subset of the N ultrasound beams. The clutter filter is then adjusted to attenuate selected echo signal data returned from the ROI that exhibits the wall motion velocity data. The wall motion data derived from the N ultrasound beams or a subset thereof is processed by the adjusted clutter filter to derive echo data that is better indicative of echo signal returns from the contrast agent or blood flow and is less indicative of wall motion effects.

15 Claims, 5 Drawing Sheets

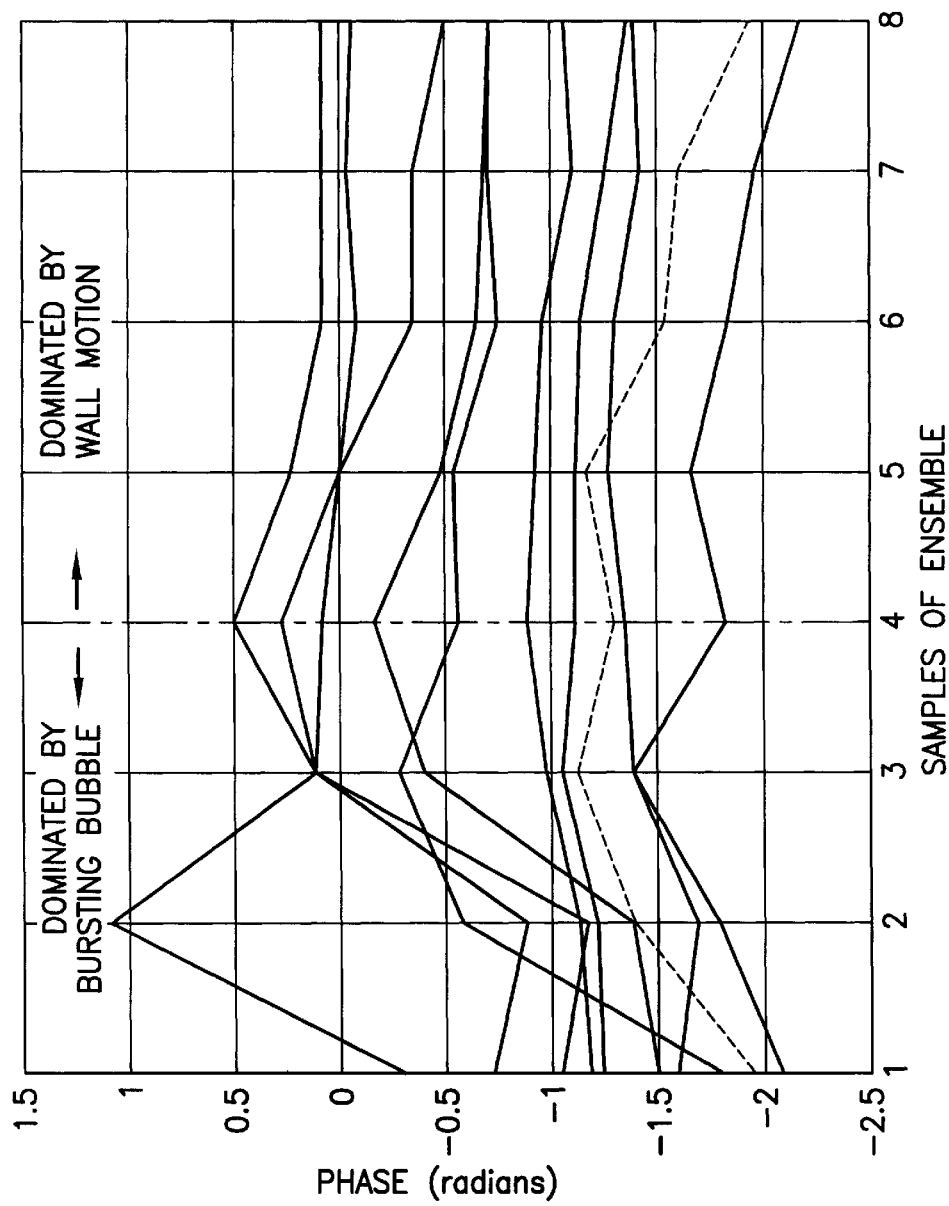

ULTRASONIC METHOD USING ADAPTIVE CLUTTER FILTER TO REMOVE TISSUE WALL MOTION

FIELD OF THE INVENTION

This invention relates to ultrasonic imaging of a contrast agent in an anatomical region and, more particularly, to a method for adjusting an adaptive clutter filter to reject tissue wall motion so as to leave echoes from the contrast agent as the predominant return signal.

BACKGROUND OF THE INVENTION

Current ultrasonic imaging systems make use of contrast agents in circulation to enhance ultrasound returns. Contrast agents are substances which strongly interact with ultrasound waves and return echoes which may be clearly distinguished from those returned by blood and tissue. Microbubbles are currently employed as a contrast agent and provide a non-linear behavior in certain acoustic fields. Microbubble contrast agents are useful for imaging of the body's vascular system and are injectable through the veins and arteries. They are subsequently filtered from the blood stream by the lungs, kidneys and liver.

Microbubble contrast agents generally comprise coated gas bubbles that are stable in the body for a significant period of time. The coating shells serve to protect the gas from diffusion into the blood stream. At moderately high ultrasound pressure amplitudes, the shells of the microbubbles can be caused to rupture, freeing the internal gas and substantially reducing the detectability thereof by incident ultrasound waves.

U.S. Pat. No. 5,833,613 to Averkiou et al. discloses an ultrasound method for imaging of contrast agents. In one embodiment, a rate of re-perfusion of an anatomical region is accomplished by initially destroying the contrast agent within the region, and then subsequently imaging the region to determine the rate of re-insertion of the contrast agent.

U.S. Pat. No. 5,546,257 to Johnson et al. describe an ultrasonic system that detects and destroys microbubble contrast agent in circulation. The microbubble destruction is detected by phase insensitive detection and differentiation of echoes received from two consecutive ultrasonic transmissions.

When a region containing contrast agent is irradiated with a high energy ultrasound beam, the destruction of the contrast agent results in relatively high amplitude echo signals being returned to the receiving chain of the ultrasound unit. However, during such action, the echo returns from wall motion may be of an equal or higher amplitude. Such wall motion signals can mask or otherwise impair the signal from the contrast agent.

The prior art has utilized adaptive clutter filtering to determine the velocity of highest power echo signals, usually tissue. The adaptive clutter filter is then controlled so as to center its maximum attenuation at the determined velocity (from Doppler processing) so as to suppress tissue wall motion. The leftover signals are, in the main, those returned from blood flow.

This approach works well for conventional color flow imaging (CFMI) because signals from wall motion are often significantly higher in power than any other color flow signal of interest. Thus, the control processor could be assured of properly adjusting the frequency attenuation characteristic of the adaptive clutter filter if it set the filter to track the frequency of largest amplitude echo signals.

However, contrast agents, when destroyed provide a high power echo signal that exhibits chaotic phase characteristics. Thus when a standard adaptive clutter filter is caused to lock onto the signal echoes from the microbubble destruction due to their high energy, such action can cause the filter to place maximum attenuation on the microbubble destruction signal frequencies rather than the wall motion that is sought to be attenuated.

Accordingly, There is a need for an improved method for displaying to the user an image that evidences enhanced characteristics from microbubble contrast agent destruction. Further, a method is required that efficiently removes tissue wall motion echo returns so as to enable improved contrast agent display specificity

SUMMARY OF THE INVENTION

The method of the invention controls an ultrasound system that implements a clutter filter, to derive parameters such as blood flow velocity, echo power and/or echo amplitude data from an anatomical region of interest (ROI) that includes both a blood flow region and a tissue wall region and into which a contrast agent has been introduced. The method initially transmits an ensemble of N ultrasound beams along a common azimuth and elevation into the ROI to cause dest ruction of the contrast agent lying along the azimuth. Estimated wall motion velocity data is then derived for the tissue wall region through use of selected echo signal data derived from a subset of the N ultrasound beams of the ensemble, the subset excluding echo signal data from a first M of the N ultrasound beams or any subset of the N ultrasound beams. The clutter filter is then adjusted to attenuate selected echo signal data returned from the ROI that exhibits the wall motion velocity data. The wall motion data derived from the N ultrasound beams or a subset thereof is processed by the adjusted clutter filter to derive echo data that is better indicative of echo signal returns from the contrast agent or blood flow and is less indicative of wall motion effects.

BRIEF DESCRIPTION OF THE DRAWINGS

FIG. 4 is a plot of phase variation of echo signals across an ensemble of transmitted beams.

DETAILED DESCRIPTION OF THE PREFERRED EMBODIMENT

During the following description of the invention, it will be assumed that ultrasound system 10 (see FIG. 1) has been adjusted so as to image a ROI within a patient's anatomy. Prior to or during a scan of the ROI, a contrast agent is introduced into the blood stream. Next, an ensemble of N high power ultrasound beams is transmitted along a common azimuth and elevation to destroy the contrast agent along the beam path. The Doppler echo values for each of the N beams are then processed, digitized and stored as respective lines of Doppler data (i.e., magnitude and phase) for each beam.

Excluding the first M of the N lines (or any subset of the N lines), a set of (N-M) lines of digital echo values are then used to derive an estimated wall motion velocity for each image element. As will be hereafter understood, the exclusion of the first M lines of echo data eliminates most of the echo returns experienced from the bursting microbubbles. This action allows the wall motion velocity to be determined from echo data for each picture element from the latter echo data lines, where the data is dominated by wall motion returns rather than by the high power returns from the contrast agent. More particularly, after the first M lines of echo returns have been received, the majority of the contrast bubbles have been destroyed and the thereafter echo return data from the contrast bubbles is greatly reduced, leaving the wall motion velocity data to predominate.

The derived data is then used to calculate an estimate of wall motion velocity which is, in turn, used to set up an adaptive clutter filter to attenuate estimated echo data values that exhibit frequency characteristics in accord with determined wall velocities. All N lines (or a subset thereof) of digital Doppler echo values are processed through the adjusted adaptive clutter filter. The resultant output from the adaptive clutter filter is, in the main, blood flow or contrast agent signal with minimized wall signal contribution.

Parameters such as blood flow velocities, echo signal powers and amplitudes are then derived from the blood flow data and color attributes are assigned accordingly.

Figure 1:
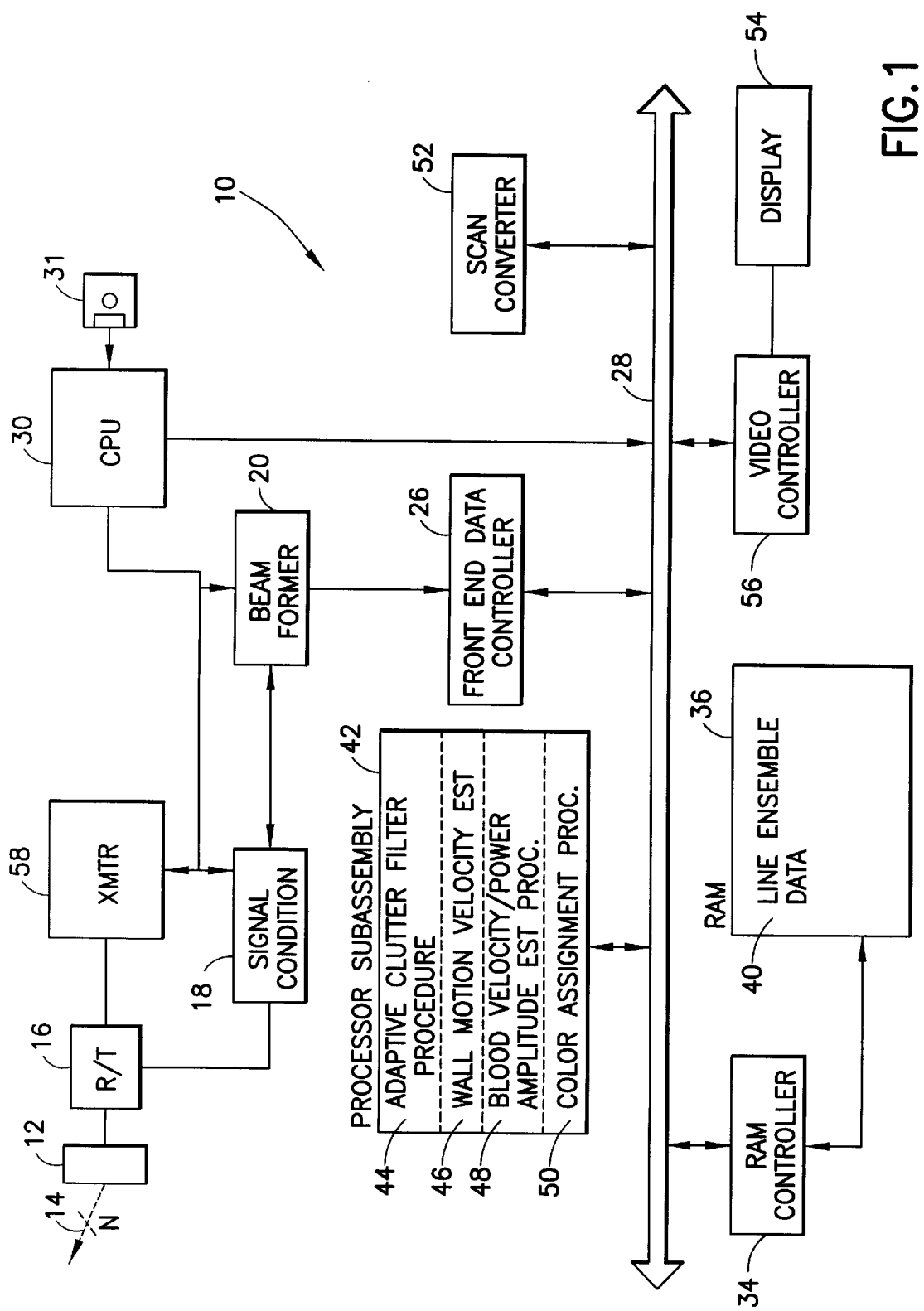
FIG. 1 is a high-level block diagram of an ultrasound imaging system incorporating the invention.

Referring now to FIG. 1, ultrasound system 10 includes a transducer 12 that, in the known manner, outputs an ultrasound beam 14 at a plurality of predetermined scan azimuths, elevations and focal depths. In this invention, transducer 12 is further controlled to transmit a plurality (i.e., an "ensemble") of ultrasound beams at each azimuth and elevation, at a power level that is sufficient to destroy microbubble contrast agent that has been introduced into an ROI being imaged. Echo signals are sensed by transducer 12 and are fed through a receive/transmit switch 16 to a signal conditioner 18 and, in turn, to a beamformer 20. Signal conditioner 18 receives the echo ultrasound analog signals and conditions those signals by amplification and forming circuitry, prior to their being fed to beamformer 20. Within beamformer 20, the ultrasound signals corresponding to each transmitted beam are converted to "lines" of digital data values.

Beamformer 20 feeds the lines of digital data values to a front end data controller 26 which, in turn, transmits that data via bus 28 to a RAM controller 34. RAM controller 34, in turn, stores the lines of digital data in random access memory (RAM) 36 in line ensemble data region 40.

At this stage, the line ensemble data is further processed to enhance the return signal values from the contrast agent versus return signal values from tissue regions and, more particularly, from wall motion artifacts. Within a processor subassembly 42 resides a number a code sequences that enable the provision of such signal value enhancements. In particular, an adaptive clutter procedure 44 enables the line ensemble data to be filtered so as to exclude signals having indicated velocities that result from wall motion returns. Processor subassembly 42 further includes a wall motion velocity estimator procedure 46 that is adapted to analyze the line ensemble data and to estimate therefrom, the actual velocity of the wall motion. A blood velocity/power/ amplitude estimation procedure 48 is used to analyze the output data from adaptive clutter filter procedure 44 and to assign velocity, power levels and/or amplitudes to the resulting data. Finally, a color assignment procedure 50 is utilized to selectively assign color values to picture elements having velocity and power values that lie within common ranges.

Figure 3:
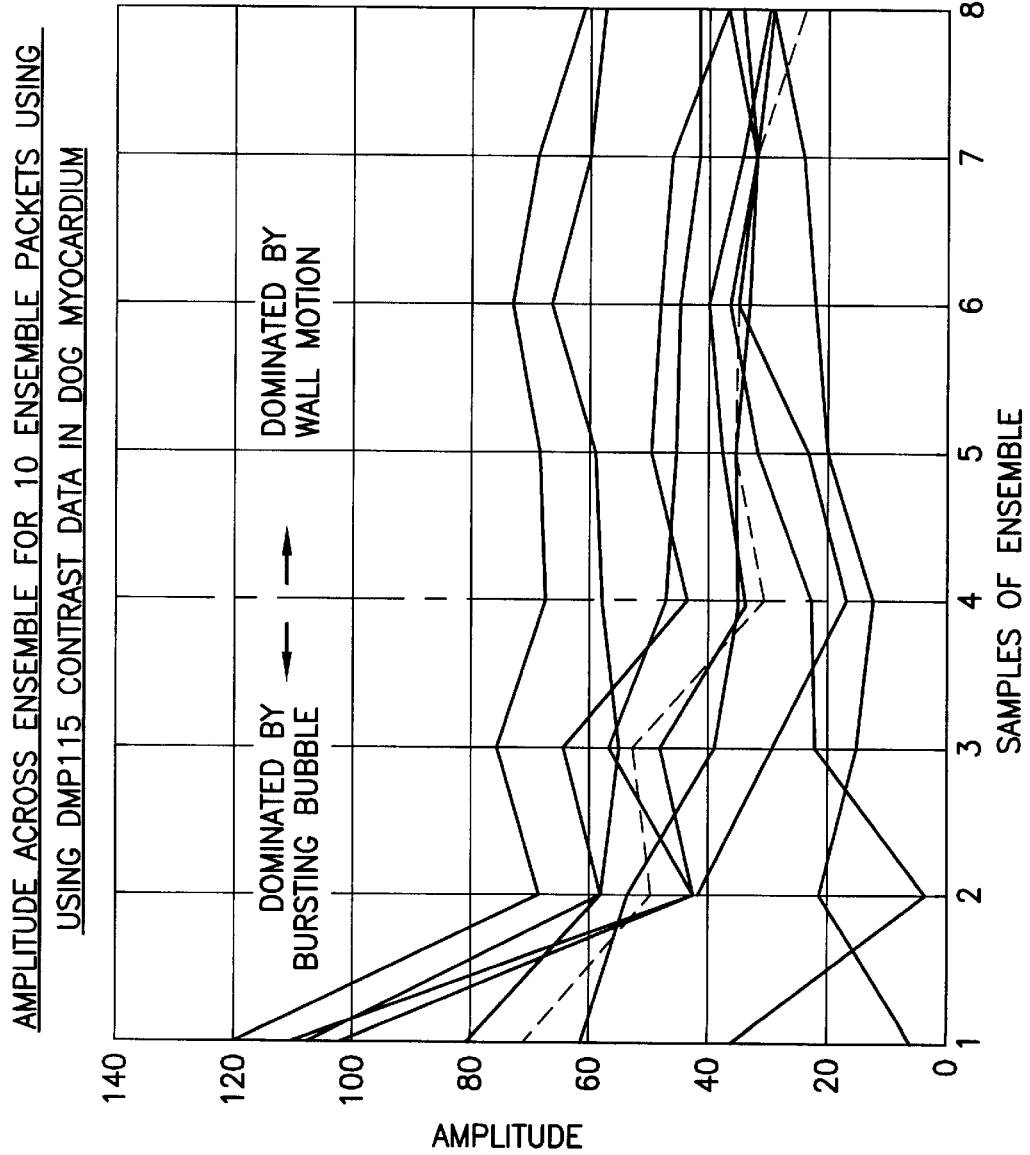
FIG. 3 is a plot of amplitude variation of echo signals across an ensemble of transmitted beams.

As indicated above, a principal object of this invention is to improve the imaging of microbubble contrast agent and to remove tissue wall motion artifacts from the presentation. Referring briefly to FIGS. 3 and 4, FIG. 3 illustrates a plot of echo signal amplitude per line of an ensemble. Note that for lines 1–3, that there is significant variation in amplitude that is due, in the main, to the effects of the bursting microbubbles on the incident ultrasound signals. However, from line 4 of the ensemble and forward in time, the echo signal amplitudes are largely due to the wall motion. This is due to the destruction of the microbubbles over the period of lines 1–3.

FIG. 4 illustrates a plot of phase versus lines of an ensemble and the chaotic phase created by bursting microbubbles of lines 1–3. From line 4, forward, the phase information is dominated by tissue wall echo returns, evidencing a relatively coherent phase picture.

From the data shown in FIGS. 3 and 4, it has been determined that by ignoring the echo return data from an initial set of lines of an ensemble, enables a more accurate setting of the adaptive clutter filter to remove signals which result from the tissue wall motion. Accordingly, the output from the adaptive clutter filter then becomes more representative of the microbubble contrast agent echo returns.

Once line ensemble data 40 has been filtered by adaptive clutter filter procedure 44, that data is passed to scan converter 52 where it is converted to an appropriate format for presentation on display 54. Thereafter, the image data is passed to video controller 56 which controls display 54 to appropriately show the respectively colored images.

Figure 2A:
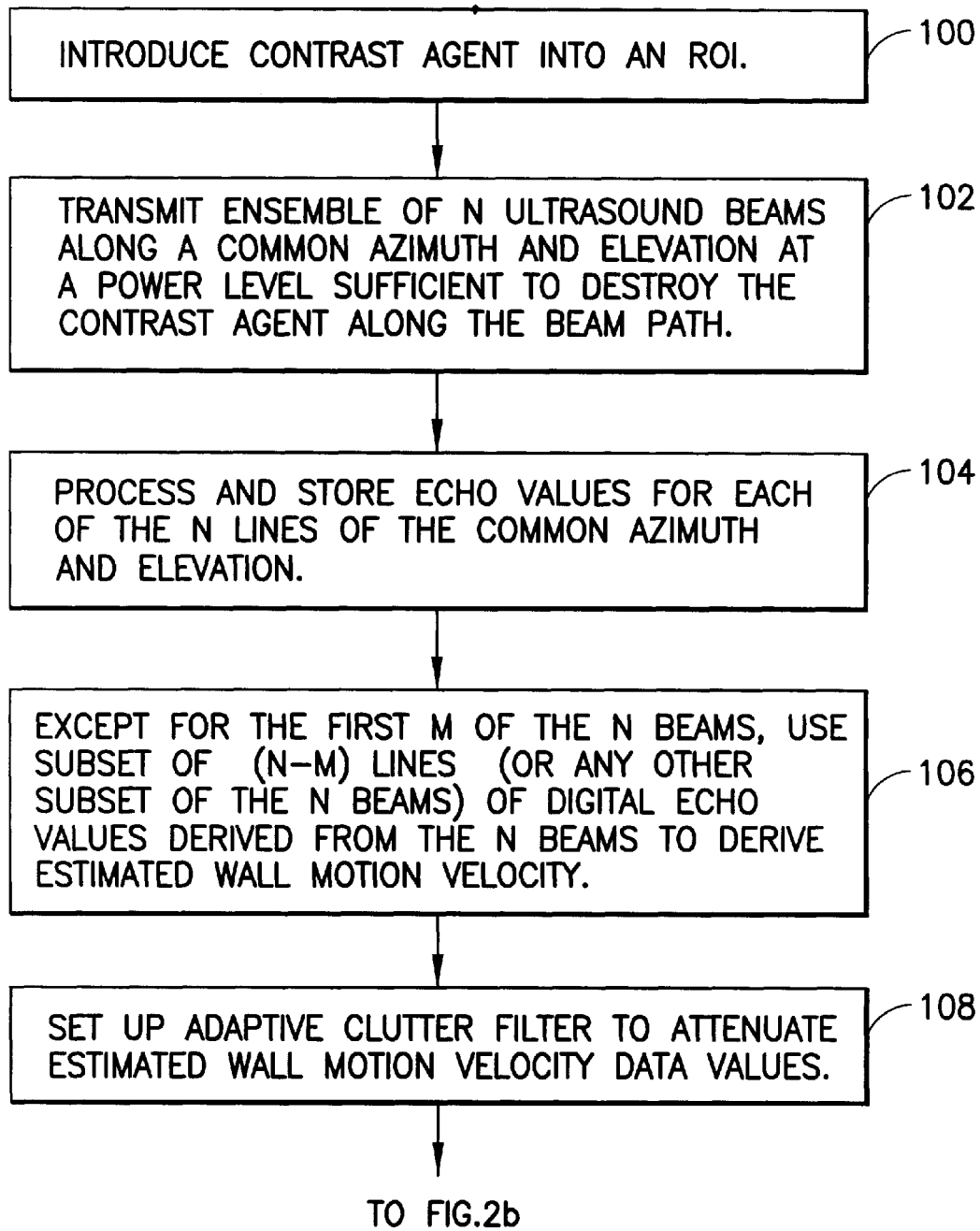
FIGS. 2a and 2b comprise a high-level, flow diagram illustrating the method of t he invention.
Figure 2B:
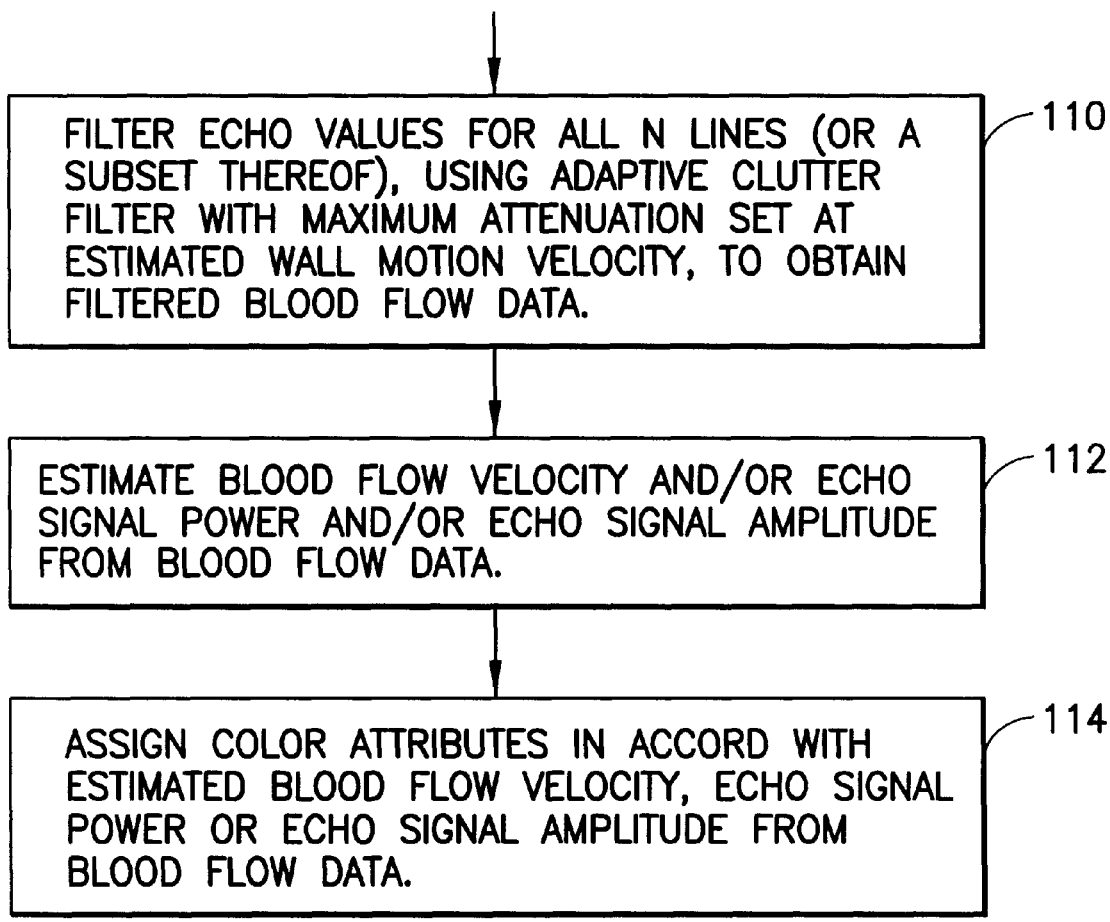

Turning now to FIGS. 2a and 2b in conjunction with FIG. 1, the method of the invention will be described. Initially, a contrast agent is introduced into a patient's circulation so as to be present in an anatomical ROI (step 100). Thereafter, CPU 30 controls transmitter 58 to output signals to transducer 12 and causes the transmission of N high power ultrasound beams along a common azimuth 14. This action is repeated for all azimuths and elevations of scan. The ultrasound beams have sufficient power to apply a level of acoustic energy to the circulating microbubble contrast agent to cause destruction thereof along the beam path (step 102).

The returned echo signals from both tissue, blood and contrast agent are received by a transducer 12 and passed via receive/transmit switch 16 to signal conditioning module 18 and beam former 20. For each picture element along beam 14, both a magnitude and phase of the echo signal are derived for returns from each of the N transmitted beams of an ensemble. If it is assumed that N=10, then for each picture element, 10 signal magnitudes and phases are accumulated as a result of the transmitted ensemble of beams. That data is stored in line ensemble data region 40 in RAM 36 (step 104).

As described above, in order to achieve improved imaging of the microbubble contrast agent (and echo returns that result from the destruction thereof), it is desirable to eliminate the returns resulting from interaction of the ultrasound waveforms and tissue/boundary areas. However, as described above, the first M of the N lines exhibit both chaotic phase relationships and widely varying amplitude relationships. Therefore, to assure that the eliminated signal values are truly the result of reflections from the tissue/ boundary regions, the line data which includes microbubble contrast agent return signals is eliminated from the wall velocity estimate calculation. This assures that the remaining line data is more truly representative of signal returns from the tissue/boundary regions. It is that remaining line data that is now used to find the tissue/boundary velocity(s).

Accordingly, CPU 30 calls wall motion velocity estimator procedure 46 and supplies thereto, N-M lines of digital echo values for processing. The M lines comprise, for example, the first two or three lines of tissue echo return values which exhibit the chaotic phase and amplitude characteristics previously discussed. Wall motion velocity estimator 46, using only the latter lines of the N lines (i.e., N-M), is able to derive an accurate wall motion velocity figure from the wall motion phase data (step 106). The determined wall motion velocity is then utilized to set up adaptive clutter filter procedure 44 to attenuate velocity/frequency values about the determined wall motion velocity (step 108).

Thereafter, adaptive clutter filter procedure 44 is called and accesses the N lines (or a subset thereof) of line ensemble data 40 and processes them in accordance with the aforesaid filter setting so as to attenuate the estimated wall motion velocities and obtain the remaining blood flow data (step 110). Note that this data constitutes the microbubble contrast agent echo return data less data exhibiting wall motion velocity.

Next, blood velocity/power estimation procedure 48 is called and estimates the blood flow velocities, signal powers and/or signal amplitudes from the blood flow data that is output by adaptive clutter filter procedure 44 (step 112). Color assignment procedure 50 is then called and assigns color attributes in accordance with the estimated blood flow velocities, echo signal powers/amplitudes determined by blood velocity/power/amplitude estimation procedure 48 (step 114). The resultant outputs to display 54 are, as a result, better indicative of the signal returns from the microbubble contrast agent, than would otherwise occur if the masking tissue/wall motion returns were still present in the echo data.

It should be understood that the foregoing description is only illustrative of the invention. Various alternatives and modifications can be devised by those skilled in the art without departing from the invention. For example, while the procedures required to perform the method of the invention have been described as being already loaded into RAM or present in memory on processor subassembly 42, they may be stored on a memory device 31 (FIG. 1) and loaded on an as-needed basis. Further, the invention may also be carried out through use of harmonic return signals as well as fundamental return signals. Accordingly, the present invention is intended to embrace all such alternatives, modifications and variances which fall within the scope of the appended claims.

What is claimed is:

1. A method for controlling an ultrasound system that implements clutter filter means, to derive blood flow velocity, echo power data or echo amplitude data from an anatomical region of interest (ROI) and into which a contrast agent has been introduced, said method comprising the steps of:
   a) transmitting an ensemble of N ultrasound beams along a common azimuth and elevation into said ROI to cause destruction of said contrast agent lying along said azimuth and elevation;
   b) deriving estimated wall motion velocity data for a tissue wall region through use of selected echo signal data derived from a subset of said N ultrasound beams of said ensemble, said subset excluding echo signal data from M of said N ultrasound beams;
   c) adjusting said clutter filter means to attenuate selected echo signal data returned from said ROI exhibiting said wall motion velocity data; and
   d) subjecting wall motion data derived from said N ultrasound beams, or a subset thereof, to said clutter filter means, adjusted according to step c, to derive echo data that is better indicative of echo signal returns from said contrast agent.

2. The method as recited in claim 1, comprising the further step of:
   e) deriving power or amplitude data corresponding to echo data that results from step d) and assigning attributes to said echo data in accord with said power or amplitude data.

3. The method as recited in claim 2, wherein each of said attributes is a different color.

4. The method as recited in claim 1, comprising the further step of:
   e) deriving blood flow velocity data corresponding to echo data that results from step d) and assigning attributes to said echo data in accord with said blood flow velocity data.

5. The method as recited in claim 4, wherein each of said attributes is a different color.

6. The method as recited in claim 1, wherein said contrast agent comprises microbubbles of an encapsulated gas.

7. A memory media for controlling an ultrasound system that implements clutter filter means, to derive blood flow velocity, echo power data or echo amplitude data from an anatomical region of interest (ROI) and into which a contrast agent has been introduced, said memory media comprising:
   a) means for controlling said ultrasound system to transmit an ensemble of N ultrasound beams along a common azimuth and elevation into said ROI to cause destruction of said contrast agent lying along said azimuth and elevation;
   b) means for controlling said ultrasound system to derive estimated wall motion velocity data for a tissue wall region through use of selected echo signal data derived from a subset of said N ultrasound beams of said ensemble, said subset excluding echo signal data from M of said N ultrasound beams;
   c) means for controlling said ultrasound system to adjust said clutter filter means to attenuate selected echo signal data returned from said ROI exhibiting said wall motion velocity data; and
   d) means for controlling said ultrasound system to subject wall motion data derived from said N ultrasound beams, or a subset thereof, to said clutter filter means, as adjusted by means c), to derive echo data that is better indicative of echo signal returns from said contrast agent.

8. The memory media as recited in claim 7, further comprising:
   e) means for controlling said ultrasound system to derive power or amplitude data corresponding to echo data that results from operation of means d) and to assign attributes to said echo data in accord with said power or amplitude data.

9. The memory media as recited in claim 8, wherein each of said attributes is a different color.

10. The memory media as recited in claim 7, comprising the further step of:
   e) means for controlling said ultrasound system to derive blood flow velocity data corresponding to echo data that results from operation of means d) and to assign attributes to said echo data in accord with said blood flow velocity data.

11. The memory media as recited in claim 10, wherein each of said attributes is a different color.

12. The memory media as recited in claim 7, wherein said contrast agent comprises microbubbles of an encapsulated gas.

13. A method for removing tissue wall motion artifacts from echo data from an anatomical region of interest (ROI) into which a contrast agent has been introduced, said method comprising the steps of:
- a) deriving, from an ensemble of N ultrasound beams transmitted into said ROI to cause destruction of said contrast agent, estimated wall motion velocity data for a tissue wall region through use of selected echo signal data derived from a subset of said N ultrasound beams of said ensemble, said subset excluding echo signal data from M of said N ultrasound beams;
- b) adjusting said clutter filter means to attenuate selected echo signal data returned from said ROI exhibiting said wall motion velocity data; and
- c) subjecting wall motion data derived from said N ultrasound beams, or a subset thereof, to said clutter filter means, adjusted according to step b, to derive echo data that is better indicative of echo signal returns from said contrast agent.

14. A memory media for controlling an ultrasound system to remove tissue wall motion artifacts from echo data from an anatomical region of interest (ROI) into which a contrast agent has been introduced, said ultrasound system incorporating clutter filter functionality, said memory media comprising:
- a) means for controlling the ultrasound system to derive, from an ensemble of N ultrasound beams transmitted into said ROI to cause destruction of said contrast agent, estimated wall motion velocity data for a tissue wall region through use of selected echo signal data derived from a subset of said N ultrasound beams of said ensemble, said subset excluding echo signal data from M of said N ultrasound beams;
- b) means for controlling the ultrasound system to adjust said clutter filter functionality to attenuate selected echo signal data returned from said ROI exhibiting said wall motion velocity data; and
- c) means for controlling the ultrasound system to subject wall motion data derived from said N ultrasound beams, or a subset thereof, to said clutter filter functionality, adjusted by means b), to derive echo data that is better indicative of echo signal returns from said contrast agent.

15. A method for controlling an ultrasound, said method comprising the steps of:
- adjusting a clutter filter to attenuate selected echo signal data returned from a ROI exhibiting wall motion velocity data derived from a subset of N ultrasound beams of an ensemble of ultrasound beams, said subset excluding echo signal data from M of said N ultrasound beams; and
- subjecting the wall motion, or a subset thereof, to the adjusted clutter filter to derive echo data that is better indicative of echo signal returns from a contrast agent in the ROI.

* * * * *